(12) United States Patent
Shiohama (10) Patent No.: US 10,332,733 B2
(45) Date of Patent: Jun. 25, 2019

(54) TANDEM MASS SPECTROMETER

(71) Applicant: SHIMADZU CORPORATION, Kyoto-shi, Kyoto (JP)

(72) Inventor: Tohru Shiohama, Osaka (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/747,465

(22) PCT Filed: Jul. 28, 2015

(86) PCT No.: PCT/JP2015/071382
§ 371 (c)(1),
(2) Date: Jan. 25, 2018

(87) PCT Pub. No.: WO2017/017787
PCT Pub. Date: Feb. 2, 2017

(65) Prior Publication Data
US 2018/0218893 A1 Aug. 2, 2018

(51) Int. Cl.
*H01J 49/00* (2006.01)
*G01N 27/62* (2006.01)
*H01J 49/06* (2006.01)
*H01J 49/42* (2006.01)

(52) U.S. Cl.
CPC .......... *H01J 49/0072* (2013.01); *G01N 27/62* (2013.01); *H01J 49/005* (2013.01); *H01J 49/0027* (2013.01); *H01J 49/063* (2013.01); *H01J 49/4215* (2013.01); *H01J 49/4225* (2013.01)

(58) Field of Classification Search
CPC ....... H01J 49/0031; H01J 49/005; H01J 49/04
USPC ....... 250/281, 282, 283, 286, 287, 290, 293, 250/294, 396 R
See application file for complete search history.

(56) References Cited

U.S. PATENT DOCUMENTS 8,866,074 B2 * 10/2014 Okumura ............ H01J 49/0031
250/281
2011/0049351 A1 * 3/2011 Zabrouskov ....... G01N 33/6848
250/282

FOREIGN PATENT DOCUMENTS

JP 2014-165053 A 9/2014

OTHER PUBLICATIONS

International Search Report of PCT/JP2015/071382 dated Oct. 27, 2015.
(Continued)

*Primary Examiner* — David A Vanore
(74) *Attorney, Agent, or Firm* — Sughrue Mion, PLLC (57) ABSTRACT

A precursor ion selected by a quadrupole mass filter is fragmented by imparting a predetermined amount of collision energy (CE) to the ion. Among the thereby generated product ions, only the ions included within a predetermined m/z range are stored in an ion trap. The ions are subsequently separated and detected by a TOF. For one precursor ion originating from a target compound, a mass spectrometric analysis is performed for each combination of a plurality of the set CE values and subdivided m/z ranges to obtain spectrum data. A spectrum data accumulator accumulates the spectrum data obtained by the mass spectrometric analysis under different combinations of (CE value, m/z range). Based on the accumulated spectrum data, a mass spectrum creator creates a single product-ion spectrum corresponding to the target compound.

6 Claims, 3 Drawing Sheets

(56) References Cited

OTHER PUBLICATIONS

Written Opinion dated Oct. 27, 2015 in application No. PCT/JP2015/071382.

* cited by examiner

Fig. 1

TANDEM MASS SPECTROMETER

CROSS REFERENCE TO RELATED APPLICATIONS

This application is a National Stage of International Application No. PCT/JP2015/071382 filed Jul. 28, 2015, the contents of which are incorporated herein by reference in its entirety.

TECHNICAL FIELD

The present invention relates to a tandem mass spectrometer for fragmenting an ion having a specific mass-to-charge ratio m/z by collision-induced dissociation (CID) or similar processes, and for performing a mass spectrometric analysis of the thereby generated product ions (fragment ions).

BACKGROUND ART

An MS/MS analysis (tandem analysis), which is a technique of mass spectrometry, is a useful technique for identifying a high-molecular compound and/or analyzing its chemical structure. In recent years, this technique has been widely used in various areas. A structural analysis of a target compound using an MS/MS analysis is normally performed as follows: An ion having a specific mass-to-charge ratio originating from the target compound is selected as a precursor ion from various kinds of ions generated from a sample. The precursor ion is fragmented by an appropriate technique, such as making the precursor ion collide with CID gas. The thereby generated product ions are separated according to their mass-to-charge ratios and detected. Based on the detection signals, a mass spectrum (product-ion spectrum) which shows the relationship between the mass-to-charge ratios of the product ions and their intensities is obtained. The chemical structure of the target compound is estimated from the peak pattern of the product ions observed in the mass spectrum. In some cases, a neutral loss determined from the difference in mass-to-charge ratio between two peaks may also be used for the estimation.

A commonly known type of mass spectrometer for MS/MS analysis is a triple quadrupole mass spectrometer including two quadrupole mass filters respectively placed before and after a collision cell in which the CID process is performed. A so-called Q-TOF mass spectrometer, which can be obtained by replacing the rear quadrupole mass filter in the triple quadrupole mass spectrometer with a time-of-flight mass spectrometer, is more complex in structure and more expensive than the triple quadrupole mass spectrometer, yet has the advantage of being capable of acquiring more accurate mass spectra. In the present description, a mass spectrometer having two mass analyzers respectively placed before and after a collision cell is called the "tandem mass spectrometer".

As is commonly known, various bonding sites in a compound have different levels of bond energy, so that those bonding sites also vary in ease of breakage. Therefore, if the collision energy which is determined, for example, by the voltage difference between a DC bias voltage applied to the front quadrupole mass filter and a DC bias voltage applied to an ion guide placed within the collision cell is changed in a tandem mass spectrometer, the fragmentation occurs in different forms even if the precursor ion originates from the same compound. In general, for an analysis of the chemical structure of a complex compound, it is convenient to have information on the masses of a wider variety of fragments (product ions and neutral losses) originating from the compound. Accordingly, in a conventionally known technique, a mass spectrometric analysis of the product ions is repeated for the same compound while changing the amount of collision energy to a plurality of levels. The obtained mass spectra are accumulated or averaged to create a mass spectrum in which a larger number of kinds of product ions can be observed, and a qualitative determination or structural analysis is performed using this mass spectrum.

A mass spectrometer described in Patent Literature 1 has been known as a device for obtaining, with a small number of analyses, a mass spectrum in which various kinds of product ions produced by fragmentation under different levels of collision energy can be observed. In this mass spectrometer, an ion trap for temporarily capturing ions is placed between a collision cell and a rear mass separator (time-of-flight mass analyzer). Product ions generated by fragmentation at different points in time under different levels of collision energy are temporarily stored in the ion trap. The stored ions are simultaneously ejected from the ion trap and subjected to mass spectrometry by the time-of-flight mass analyzer to obtain a mass spectrum. By this technique, a mass spectrum which shows various product ions that have resulted from fragmentation under different levels of collision energy, i.e. which have been obtained in various modes of fragmentation, can be obtained by a single mass spectrometric operation in the time-of-flight mass analyzer.

CITATION LIST

Patent Literature

Patent Literature 1: JP 2014-165053 A

SUMMARY OF INVENTION

Technical Problem

As just described, the mass spectrometer described in Patent Literature 1 has the advantage that a mass spectrum in which many kinds of product ions are observed can be obtained by a single mass spectrometric operation in a time-of-flight mass analyzer.

Such a mass spectrometer requires the largest possible amount of ions to be stored in the ion trap for mass spectrometry in order to improve the detection sensitivity for the ions in the mass spectrum. In the case of a linear ion trap which captures ions within a long space extending along a longitudinal axis surrounded by a plurality of rod electrodes (normally, four rod electrodes) arranged parallel to each other, a comparatively large amount of ions can be stored since the ion-storage space is large. By comparison, in the case of a three-dimensional quadrupole ion trap which includes an annular ring electrode and a pair of endcap electrodes facing each other across the ring electrode, the ion-storage space is small, and the amount of ions that can be stored is considerably limited due to the space charge effect. If the number of kinds of product ions is comparatively small, three-dimensional quadrupole ion traps can generate signals with sufficiently high intensity per one product ion. However, the number of kinds of product ions normally increases with an increase in the complexity of the chemical structure of the compound, causing the signal intensity per one product ion to be lower. Accordingly, three-dimensional quadrupole ion traps are less advantageous for qualitative determination or structural analyses.

The present invention has been developed to solve such a problem. Its objective is to provide a tandem mass spectrometer capable of obtaining a mass spectrum in which many kinds of product ions originating from one compound can be observed with high sensitivity, thereby improving the accuracy of qualitative determination or structural analysis of the compound.

Solution to Problem

The first aspect of the present invention developed for solving the previously described problem is a tandem mass spectrometer including: an ion source for ionizing a compound in a sample; a first mass separation section for selecting, as a precursor ion, an ion having a specific mass-to-charge ratio from various kinds of ions generated by the ion source; an ion fragmentation section for fragmenting the precursor ion by collision-induced dissociation; and a second mass separation section and a detector for performing a mass spectrometric analysis of various product ions generated by the fragmentation, the tandem mass spectrometer capable of temporarily storing ions by making the first mass separation section, the ion fragmentation section or the second mass separation section operate as an ion storage section, or by using an ion storage section placed between the first mass separation section and the ion fragmentation section or between the ion fragmentation section and the second mass separation section, the tandem mass spectrometer including:

a) a collision energy setter for changing the collision energy imparted to the precursor ion for the collision induced dissociation in the ion fragmentation section to m levels, where m is an integer equal to or greater than two;

b) a mass-to-charge-ratio range setter for changing the mass-to-charge-ratio range of the ions to be stored in the ion storage section to n ranges shifted along the mass-to-charge-ratio direction (where n is an integer equal to or greater than two);

c) an analysis controller for setting one of the m levels of collision energy through the collision energy setter, for setting one of the n mass-to-charge-ratio ranges through the mass-to-charge-ratio range setter, and for controlling each section to perform a mass spectrometric analysis of the product ions for a predetermined precursor ion under the condition including the combination of the set level of collision energy and the set mass-to-charge-ratio range, the analysis controller further configured to control each section to perform the mass spectrometric analysis of the product ions at least one time for each of the m×n different combinations of the collision energy and the mass-to-charge-ratio range; and d) a data processor for accumulating spectrum data obtained by the mass spectrometric analysis of the product ions performed at least m×n times under the control of the analysis controller, to create one mass spectrum over a predetermined mass-to-charge-ratio range.

The second aspect of the present invention developed for solving the previously described problem is a tandem mass spectrometer including: an ion source for ionizing a compound in a sample; a first mass separation section for selecting, as a precursor ion, an ion having a specific mass-to-charge ratio from various kinds of ions generated by the ion source; an ion fragmentation section for fragmenting the precursor ion by collision-induced dissociation; and a second mass separation section and a detector for performing a mass spectrometric analysis of various product ions generated by the fragmentation, the tandem mass spectrometer capable of temporarily storing ions by making the first mass separation section, the ion fragmentation section or the second mass separation section operate as an ion storage section, or by using an ion storage section placed between the first mass separation section and the ion fragmentation section or between the ion fragmentation section and the second mass separation section, the tandem mass spectrometer including:

a) a collision energy setter for changing the collision energy imparted to the precursor ion for the collision induced dissociation in the ion fragmentation section to m levels, where m is an integer equal to or greater than two;

b) a mass-to-charge-ratio range setter for changing the mass-to-charge-ratio range of the ions to be stored in the ion storage section to n ranges shifted along the mass-to-charge-ratio direction (where n is an integer equal to or greater than two);

c) an analysis controller for setting one of the m levels of collision energy through the collision energy setter, for setting one of the n mass-to-charge-ratio ranges through the mass-to-charge-ratio range setter, and for controlling each section to perform a mass spectrometric analysis of the product ions for a predetermined precursor ion under the condition including the combination of the set level of collision energy and the set mass-to-charge-ratio range, the analysis controller further configured to combine each of the m levels of collision energy with an integer number of mass-to-charge-ratio ranges fewer than n among the n mass-to-charge-ratio ranges in such a manner that each of the n mass-to-charge-ratio ranges is selected at least one time, and to control each section to perform the mass spectrometric analysis of the product ions at least one time for each of all combinations whose number is equal to or greater than m or n, whichever is greater; and d) a data processor for accumulating spectrum data obtained by the mass spectrometric analysis of the product ions performed the number of times equal to or greater than m or n, whichever is greater, under the control of the analysis controller, to create one mass spectrum over a predetermined mass-to-charge-ratio range.

In the tandem mass spectrometer according to the present invention, the mass separation techniques used in the first and second mass separation sections are not limited to any specific techniques. As a typical example, a quadrupole mass filter may be used as the first mass separation section, while a time-of-flight mass analyzer may be used as the second mass separation section.

When the ion storage section is provided independently of the first mass separation section or other sections, the ion storage section is a three-dimensional quadrupole ion trap or linear ion trap. When the first mass separation section, ion fragmentation section or similar section should be made to function as the ion storage section, for example, predetermined voltages can be applied to the rod electrodes (or some of those rod electrodes) which constitute a multipole having four or more poles in the section, to enable the section to effectively function as an equivalent to a linear ion trap.

Regardless of whether a three-dimensional quadrupole ion trap or linear ion trap is used, the mass-to-charge-ratio range within which ions can be captured in a stable state can be varied by changing the frequency, amplitude and/or other properties of the radio-frequency voltage applied to the electrodes constituting the ion trap in order to create a radio-frequency electric field for capturing the ions.

In the tandem mass spectrometer according to the present invention, when the first mass separation section is a quadrupole mass filter while the ion fragmentation section is a collision cell, the collision energy setter can change the level of collision energy by changing the voltage difference between the DC bias voltage applied to the rod electrodes constituting the quadrupole mass filter and the DC bias voltage applied to the rod electrodes constituting the ion guide placed within the collision cell. When the ion storage section is a three-dimensional quadrupole ion trap or linear ion trap, the mass-to-charge-ratio range setter can change the range of mass-to-charge ratios of the ions to be stored by changing the frequency, amplitude and/or other properties of the radio-frequency voltages applied to the electrodes constituting the ion trap, as described earlier. Both the change in the collision energy and the change in the mass-to-charge-ratio range can be achieved by a change in voltage, and therefore, can be performed at extremely high speeds.

In the tandem mass spectrometer according to the first aspect of the present invention, the analysis controller controls each section to perform a mass spectrometric analysis of the product ions for a predetermined precursor ion for all possible combinations of the m levels of collision energy and the n mass-to-charge-ratio ranges. When a mass spectrometric analysis for the combination of one level of collision energy and one mass-to-charge-ratio range is performed, the collision energy set through the collision energy setter and the mass-to-charge-ratio range set through the mass-to-charge-ratio range setter are both fixed, and the first mass separation section is operated so that an ion having a specific mass-to-charge ratio originating from a target compound will be selected as the precursor ion.

The precursor ion selected in the first mass separation section is given a predetermined amount of collision energy and reaches the ion fragmentation section, where the ion undergoes collision-induced dissociation and are thereby fragmented into various product ions. The product ions enter the ion storage section which, for example, is located between the ion fragmentation section and the second mass separation section. The ion storage section receives the incoming product ions for a specific duration and stores those ions inside. During this ion storage period, since the collision energy and the mass-to-charge-ratio range are fixed, only such ions that fall within a specific mass-to-charge-ratio range among the specific kinds of product ions are stored in the ion storage section. After the ions have been stored for the specific duration, those ions are ejected from the ion storage section into the second mass separation section, which detects the ions after separating them according to their mass-to-charge ratios. Thus, by this single mass spectrometric analysis, a set of data which shows a spectrum of product ions generated only within a predetermined mass-to-charge-ratio range from one precursor ion by collision-induced dissociation under a specific level of collision energy is obtained. Although the ion storage section can store only a limited amount of product ions, the ions can be detected with sufficient intensities, since the mass-to-charge-ratio range is limited so that only a reasonably small number of kinds of product ions will be stored and a sufficient number of ions per one kind of product ion will be ensured.

Since the mass spectrometric analysis is similarly performed for every possible combination of the collision energy and the mass-to-charge-ratio range, the spectrum data obtained for each mass spectrometric analysis have sufficiently high ion intensities. The data processor accumulates such spectrum data and creates a product-ion spectrum covering a wide mass-to-charge-ratio range. Even when the same precursor ion is selected, the kinds and generation ratios of the resulting product ions significantly vary with a change in the level of collision energy. The tandem mass spectrometer according to the first aspect of the present invention can exhaustively detect product ions over a wide range of mass-to-charge ratios generated under different levels of collision energy. Therefore, each of the various kinds of product ions originating from one target compound will be observed with a sufficient level of sensitivity on the product-ion spectrum created by the data processor.

It should naturally be understood that the mass spectrometric analysis for one combination of the collision energy and the mass-to-charge-ratio range may be performed multiple times, if the measurement time allows. For example, each of the m×n different combinations of the collision energy and the mass-to-charge-ratio range may be executed L times (where L is an integer equal to or greater than two), and the spectrum data obtained by the mass spectrometric analysis performed m×n×L times may be accumulated to obtain a product-ion spectrum.

The tandem mass spectrometer according to the second aspect of the present invention differs from the first aspect in that the mass spectrometric analysis for at least one combination of the collision energy and the mass-to-charge-ratio range is omitted among the m×n possible combinations. This is because, if it is expected that only a few or insignificant number of product ions will be observed for a certain combination of the collision energy and the mass-to-charge-ratio range, it will be a waste of time to perform a mass spectrometric analysis under that condition. Such combinations of the collision energy and the mass-to-charge-ratio range for which no practically useful results will be obtained can be determined from preliminary measurements performed beforehand or empirical information collected from documents or similar sources. Then, the analysis controller can be configured to control each section to omit the mass spectrometric analysis of the product ions for such combinations.

Specifically, for example, in the case where setting a higher level of collision energy causes a certain kind of compound to be more easily fragmented into product ions having smaller mass-to-charge ratios product ions having small mass-to-charge ratios are less likely to be observed when a low level of collision energy is given. Accordingly, if such a phenomenon is previously known or can be predicted, the mass spectrometric analysis of the product ions for a combination of a low level of collision energy and a low mass-to-charge-ratio range can be omitted.

The omission of the mass spectrometric analysis for a combination of the collision energy and the mass-to-charge-ratio range that will not yield practically useful spectrum data allows for a reduction of the measurement time required for obtaining a product-ion spectrum that has a comparable level of quality, or an acquisition of a product-ion spectrum with a higher sensitivity using the same measurement time.

In the case where a gas chromatograph (GC) or liquid chromatograph (LC) is connected to the inlet side of a mass spectrometer to analyze compounds with the mass spectrometer after temporally separating them by a column in the chromatograph, i.e. in the case of a GC-MS or LC-MS, the duration of the introduction of one compound into the mass spectrometer is limited. Even if the component separation by the column is not performed, the duration of the introduction of one compound into the mass spectrometer will be similarly limited in the case of a flow injection analysis (FIA). In such cases, it should be particularly beneficial to employ a technique that can shorten the measurement time required for obtaining a product-ion spectrum for the target compound with high sensitivity and over a wide mass-to-charge-ratio range.

In the tandem mass spectrometer according to the second aspect of the present invention, the mass spectrometric analysis may be performed the same number of times for every combination of the collision energy and the mass-to-charge-ratio range, and the obtained results may be reflected in a single mass spectrum. Alternatively, the mass spectrometric analysis may be performed a different number of times for each combination. More specifically, if a certain combination of the collision energy and the mass-to-charge-ratio range is expected to generate a product ion which is highly important for the structural analysis of a compound, it is preferable to perform the mass spectrometric analysis a greater number of times for that combination than for other combinations to thereby allow the highly important product ion to be observed with high sensitivity.

Advantageous Effects of the Invention

The tandem mass spectrometers according to the first and second aspects of the present invention can efficiently obtain a mass spectrum in which product ions with a wide range of mass-to-charge ratios originating from one compound are observed with high sensitivity. Many pieces of fragment information related to the compound, i.e. mass information of the product ions and neutral losses, can be thereby obtained, so that the accuracy of the qualitative determination or structural analysis of the compound can be improved.

In particular, the tandem mass spectrometer according to the second aspect of the present invention can shorten the period of time required for a measurement for obtaining a mass spectrum mentioned earlier. Therefore, as in a GC-MS or LC-MS, when only a short period of time can be allotted for the measurement of the ions originating from one compound, a mass spectrum with a sufficient level of quality for a qualitative determination or structural analysis of the compound can be obtained. Accordingly, the device is also suited for a simultaneous multi-component analysis using a GC-MS or LC-MS.

DESCRIPTION OF EMBODIMENTS

Figure 1:
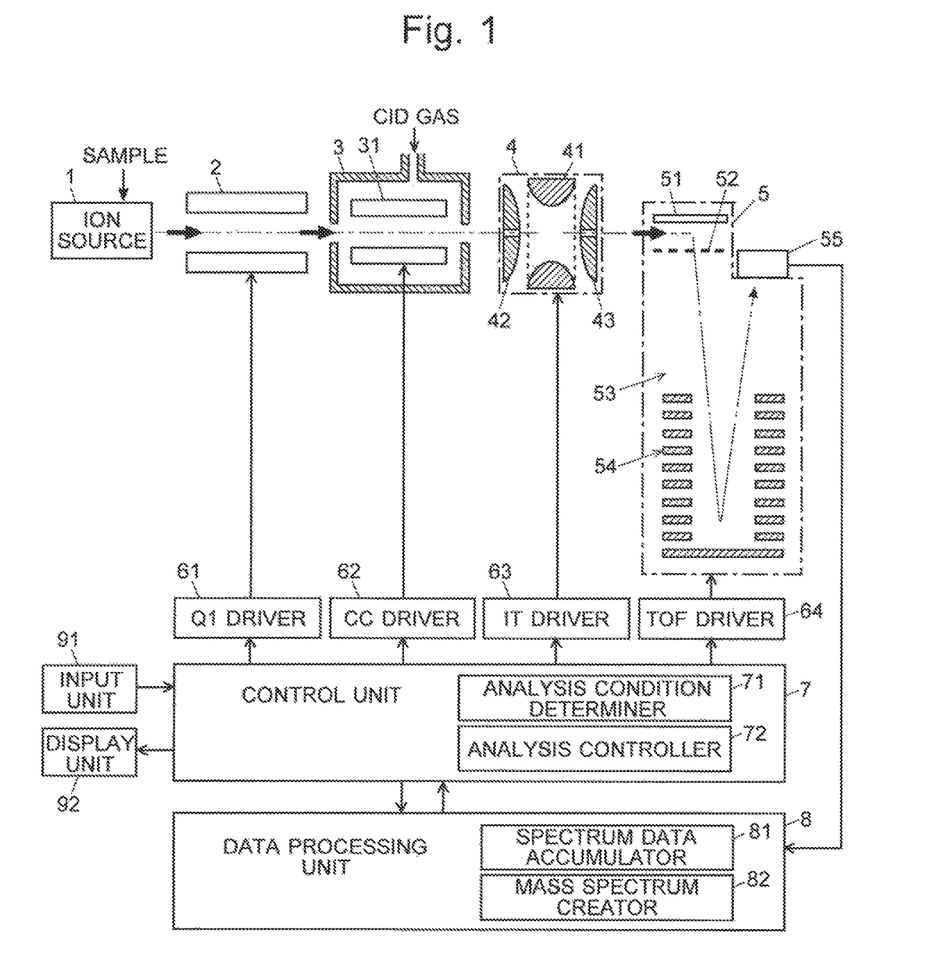
FIG. 1 is a configuration diagram of the main components of a tandem mass spectrometer as one embodiment of the present invention.

A tandem mass spectrometer as one embodiment of the present invention is hereinafter described with reference to the attached drawings. FIG. 1 is a configuration diagram of the main components of the tandem mass spectrometer according to the present embodiment. Though not shown in FIG. 1, a liquid chromatograph (LC) is connected to the inlet side of this mass spectrometer. An eluate containing a sample separated into components by a column in the LC is introduced into an ion source 1.

The tandem mass spectrometer in the present embodiment includes an ion source 1, a quadrupole mass filter 2, a collision cell 3 with an ion guide (e.g. octupole ion guide) placed inside, an ion trap 4, an orthogonal acceleration reflectron time-of-flight mass analyzer 5, and an ion detector 55, all of which are contained in a vacuum chamber (not shown). The quadrupole mass filter 2 corresponds to the first mass separation section. The collision cell 3 corresponds to the ion fragmentation section. The ion trap 4 corresponds to the ion storage section. The time-of-flight mass analyzer 5 corresponds to the second mass separation section. Ion optical devices, such as an ion guide or ion lens, for efficiently transporting ions to the subsequent section are also provided between the ion source 1 and the quadrupole mass filter 2 as well as at other appropriate locations, although those devices are omitted from FIG. 1.

Since the sample in the present embodiment is a liquid sample, the ion source 1 is an ion source employing an atmospheric pressure ionization method, such as an electrospray ionization (ESI) or atmospheric pressure chemical ionization (APCI). If the sample is a gas sample, an ion source employing an electron ionization (EI), chemical ionization (CI) or similar method can be used as the ion source 1.

The ion trap 4 has the configuration of a three-dimensional quadrupole including a pair of endcap electrodes 42 and 43 facing each other across a ring electrode 41. The ion trap 4 may be any type of ion trap that can store ions inside; for example, a linear ion trap may also be used.

The time-of-flight mass analyzer 5 includes a push-out electrode 51 and a grid electrode 52 as the orthogonal ion acceleration section, along with a reflector 54 formed by a number of reflecting electrodes arranged within a flight space 53. The time-of-flight mass analyzer 5 does not always need to be an orthogonal acceleration type. It may also be a linear or circular type instead of the reflectron type.

A Q1 driver 61 applies predetermined voltages to the rod electrodes constituting the quadrupole mass filter 2, respectively. A CC driver 52 applies predetermined voltages to the rod electrodes constituting the ion guide 31, respectively. An IT driver 63 applies predetermined voltages to the ring electrode 41 and endcap electrodes 42 and 43 constituting the ion trap 4, respectively. A TOF driver 64 applies predetermined voltages to the push-out electrode 51, grid electrode 52, reflector 54 and other elements in the time-of-flight mass analyzer 5, respectively. Those drivers 61-64 are controlled by a control unit 7. Detection signals obtained with the ion detector 55 are sampled by an analogue-to-digital converter (not shown) at predetermined intervals of time and converted into digital data, which are fed to a data processing unit 8.

The control unit 7 includes an analysis condition determiner 71 and analysis controller 72 as its functional blocks. The data processing unit 8 includes a spectrum data accumulator 81 and mass spectrum creator 82. An input unit 91 and display unit 92 as the user interface are connected to the control unit 7. Some or all of the functions included in the control unit 7 and the data processing unit 8 can normally be configured to be achieved by executing, on a personal computer (or workstation), a dedicated software program installed on the same computer.

One example of the MS/MS analysis operation performed in the tandem mass spectrometer according to the present embodiment is hereinafter schematically described.

An eluate from the column of the LC is introduced into the ion source 1. The ion source 1 ionizes the compounds contained in the introduced eluate. The ions generated from the compounds by the ion source 1 are introduced through the ion optical elements (not shown) into the quadrupole mass filter 2. Under the control of the control unit 7, the Q1 driver 61 applies, to the quadrupole mass filter 2, for example, a voltage which allows only an ion having a previously specified mass-to-charge ratio to pass through. Accordingly, among the various ions derived from the sample, an ion having the specific mass-to-charge ratio is selectively allowed to pass through the quadrupole mass filter 2 as the precursor ion.

The precursor ion is given an amount of collision energy which is determined, for example, by the potential difference between the quadrupole mass filter 2 and the ion guide 31 (or ion-injection opening of the collision cell 3), and enters the collision cell 3. Meanwhile, CID gas, such as helium or argon, is introduced into the collision cell 3. Upon coming in contact with the CID gas, the precursor ion is fragmented into product ions. The mode of this fragmentation depends on the CID conditions, such as the amount of collision energy and the pressure of the CID gas. Therefore, for example, when the amount of collision energy is changed, the kinds of product ions generated by the fragmentation as well as their amounts of generation will change even when the precursor ion is the same.

Due to the effect of the radio-frequency electric field created by the voltages applied from the CC driver 62 to the ion guide 31, the product ions travel forward while being converged, to eventually reach the ion trap 4. The product ions are introduced through an injection hole bored in the endcap electrode 42 into the inner space of the ion trap 4, and are captured within the same space due to the effect of the quadrupole electric field created by the voltage applied from the IT driver 63 to the ring electrode 41. The sequentially incoming ions are stored in the ion trap 4. After the ions are stored within the inner space of the ion trap 4 for a predetermined period of time the IT driver 63 applies a predetermined DC voltage to the endcap electrodes 42 and 43. The stored ions are thereby almost simultaneously ejected from the ion trap 4 and sent into the ion acceleration section of the time-of-flight mass analyzer 5.

At the timing when a packet of ions arrives at the ion acceleration section, the TOF driver 64 applies a predetermined voltage to the push-out electrode 51 and the grid electrode 52 to impart initial energy to each ion and thereby accelerate them in a direction substantially orthogonal to their travelling direction. The accelerated ions pass through the grid electrode 52 and enter the flight space 53. Then, due to the effect of the reflecting electric field created by the reflector 54, those ions are returned and eventually reach the ion detector 55. Ions which began their flight at almost the same point in time are separated from each other according to their mass-to-charge ratios during their flight and sequentially arrive at the ion detector 55 in ascending order of their mass-to-charge ratios. Accordingly, the data fed from the ion detector 55 to the data processing unit 8 are time-of-flight spectrum data which show the relationship between the time of flight and signal intensity, with the point of acceleration of the ions in the orthogonal acceleration section (i.e. point in time when the ions began their flight) defined as a time-of-flight value of zero. The relationship between the mass-to-charge ratio and time of flight can be determined beforehand. Based on this relationship, the time-of-flight values are converted into mass-to-charge ratios to obtain a mass spectrum from the time-of-flight spectrum.

The mass spectrum obtained in this manner is a product-ion spectrum showing the relationship between the mass-to-charge ratios and intensities of various product ions resulting from the fragmentation of a specific precursor ion. As noted earlier, a change in the level of collision energy or other CID conditions causes a change in the kinds of product ions to be obtained as well as their respective intensities. In particular, for a structural analysis of a compound, it is convenient to obtain information on the mass of various kinds of product ions originating from the compound. Accordingly, the tandem mass spectrometer according to the present embodiment is configured to allow for the setting of a plurality of levels of collision energy for generating product ions that can be reflected in a single product-ion spectrum. In other words, the device is configured so that product ions having different partial structures generated by fragmentation under a plurality of different levels of collision energy will be reflected in a single mass spectrum.

The ion trap 4 can store ions which have entered during a certain duration, and eject them in a temporally compressed form. However, due to the space charge effect, only a limited amount of ions can be stored. Furthermore, in principle, ion traps have a restriction on the range of mass-to-charge ratios that can be captured, and it is therefore difficult to exhaustively store ions over a wide mass-to-charge-ratio range. This problem is addressed in the tandem mass spectrometer according to the present embodiment as follows: The range of mass-to-charge ratios of the ions to be stored in the ion trap 4 is intentionally limited to a narrow width (specifically, about 100). This limited mass-to-charge-ratio range is shifted in a stepwise manner (along the mass-to-charge-ratio axis). The storage of the ions in the ion trap 4 and the mass spectrometric analysis for the stored ions are performed for every shift of the range. The mass spectrum data obtained by a single mass spectrometric process (including a single ejection of ions from the ion trap 4 and a mass spectrometric analysis on the ejected ions) cover only a limited mass-to-charge-ratio range. However, mass spectrum data which cover a wide mass-to-charge-ratio range can be obtained by accumulating the mass spectrum data obtained for a plurality of different mass-to-charge-ratio ranges.

Figure 2A:
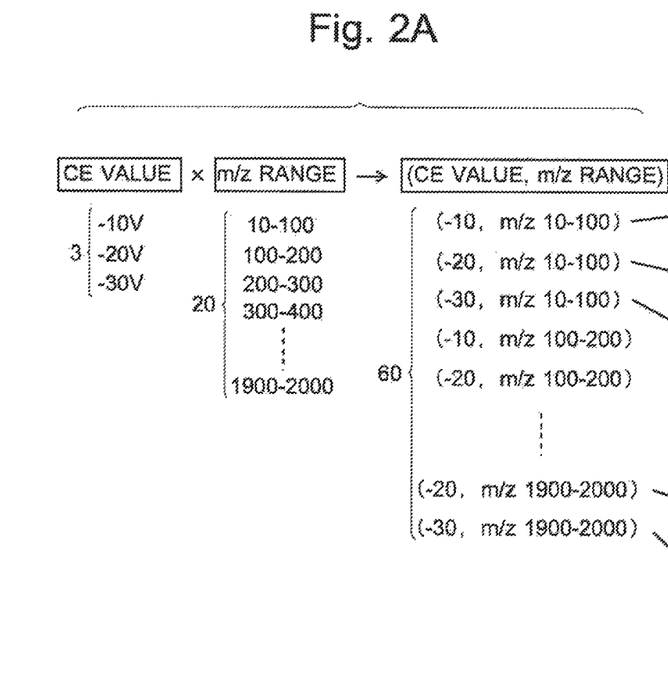
FIGS. 2A-2C are diagrams illustrating one example of the MS/MS analysis mode in the tandem mass spectrometer according to the present embodiment.
Figure 2B:
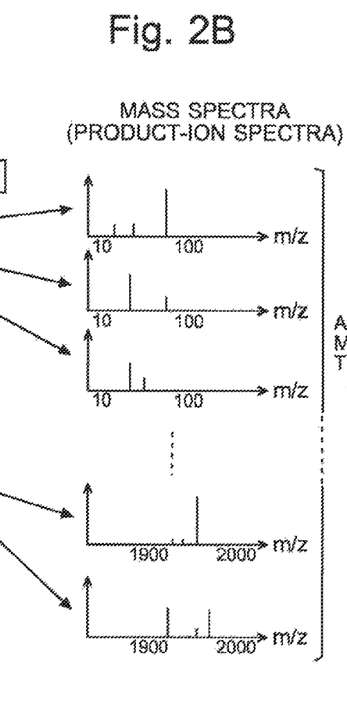
Figure 2C:
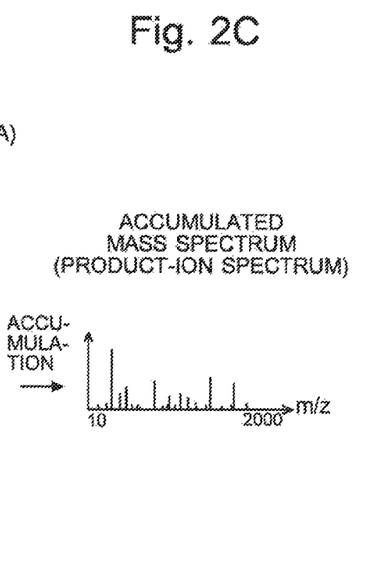

In order to obtain a mass spectrum over a wide mass-to-charge-ratio range while reflecting, in this single mass spectrum, the product ions generated by fragmentation under different levels of collision energy as mentioned earlier, the tandem mass spectrometer in the present embodiment performs an analysis in a characteristic MS/MS analysis mode, as will be hereinafter described. FIGS. 2A-2C are diagrams illustrating this MS/MS analysis mode.

In advance of an analysis, an analysis operator sets a plurality of collision-energy values (CE values) as one of the analysis conditions from the input unit 91. For example, suppose that three values have been set as the CE values: CE1, −10 V; CE2, −20 V; and CE3, −30 V. These values do not always need to be set by analysis operators; they may be previously specified as "default" values. The analysis operator also sets the entire range of mass-to-charge ratios to be subjected to the measurement from the input unit 91. For example, suppose that a range of m/z 10-2000 has been set as the entire mass-to-charge-ratio range. This range may also be previously specified as a "default" value.

The analysis condition determiner 71 divides the entire mass-to-charge-ratio range set in the previously described manner into a plurality of mass-to-charge-ratio ranges (m/z ranges) by a predetermined mass-to-charge-ratio width. For the present case, suppose that the mass-to-charge-ratio width is 100, and the entire range is divided into 20 m/z ranges: 10-100, 100-200, 200-300, . . . , 1800-1900 and 1900-2000. Subsequently, the analysis condition determiner 71 determines all possible combinations of the set CE values and m/z ranges. Let one combination of the CE value and m/z range be expressed as (CE value, m/z range). As shown in FIG. 2A, 3×20=60 independent combinations, i.e. different combinations of the CE value and m/z range, can be obtained:

(−10, m/z 10-100), (−20, m/z 10-100), (−30, m/z 10-100), (−10, m/z 100-200), (−20, m/z 100-200), . . . , (−10, m/z 1900-2000), (−20, m/z 1900-2000) and (−30, m/z 1900-2000).

The analysis condition determiner 71 additionally defines, as one cycle, the period of time in which a mass spectrometric analysis (MS/MS analysis) is performed one time under each of the 60 combinations of (CE value, m/z range), and prepares a measurement method for performing N cycles of analyses for one compound. Increasing the number of cycles is preferable for obtaining a high-sensitivity mass spectrum. However, increasing the number of cycles also unfavorably increases the measurement time. To deal with such a situation, the analysis operator may be allowed to manually set the number N of repetitions of the cycle. Otherwise, for example, if the allowable measurement time for one compound is predetermined, the number of executable cycles can be automatically computed from the allowable measurement time and the length of time required for one mass spectrometric analysis. In particular, in the case of analyzing the compounds in a sample separated into components with the column in the LC or GC, the duration of the introduction of one compound into the ion source 1 changes depending on the separation conditions in the LC or GC, and it is therefore necessary to set an appropriate number of cycles considering the duration of the introduction of the target compound into the ion source 1.

The period of time required for one mass spectrometric analysis may be constantly set independently of the m/z range. However, since an ion having a smaller mass-to-charge ratio has a shorter time of flight, it is practically possible to decrease the period of time allotted to one mass spectrometric analysis as the m/z range becomes closer to the lower mass-to-charge-ratio side. Accordingly, the period of time allotted to one mass spectrometric analysis can be varied depending on the m/z range so as to increase the number N of cycles while maintaining the measurement time for one compound.

If the target compound is known, the time at which the target compound is introduced into the ion source 1 (i.e. retention time) and the mass-to-charge ratio of the precursor ion to be selected by the quadrupole mass filter 2 can be set as one of the analysis conditions. In that case, the measurement method can be determined so that an analysis for the precursor ion will be performed for a predetermined period of time after a predetermined length of time has passed since the beginning of the analysis. In the case of identifying an unknown compound in a sample or obtaining information concerning the structure of that compound, the retention time for the compound is unknown. In such a case, the measurement method can be determined so that a normal mode of mass spectrometric analysis with no selection or fragmentation of the precursor ion is repeated at predetermined intervals of time, and upon detection of a significant peak on a mass spectrum obtained in real time, the analysis is immediately switched to a mode in which an MS/MS analysis for the detected peak is performed. Such a function is commonly known, for example, as an automatic MS$^n$.

When the analysis is initiated, the analysis controller 72 conducts the analysis according to the measurement method determined by the analysis condition determiner 71. Consider the case where the target compound is known. During the period of time in which the target compound is being introduced into the ion source 1, an ion having a specific mass-to-charge ratio originating from the target compound is selected as the precursor ion by the quadrupole mass filter 2 and is fragmented under a predetermined level of collision energy (e.g. CE1=−10V) in the collision cell 3. Various product ions thereby generated are stored in the ion trap 4, where only the ions within a predetermined mass-to-charge-ratio range (e.g. m/z range=m/z 10-100) are stored in the ion trap 4; the other ions are excluded. The product ions stored in this manner within a specific mass-to-charge-ratio range having a narrow mass-to-charge-ratio width are separated by the time-of-flight mass analyzer 5 according to their mass-to-charge ratios and detected by the ion detector 55.

The time-of-flight spectrum data fed to the data processing unit 8 for one mass spectrometric analysis only reflect product ions corresponding to one collision-energy value and one mass-to-charge-ratio range. Accordingly, if a mass spectrum were created from those time-of-flight spectrum data, the mass spectrum would cover a narrow mass-to-charge-ratio range, as shown in FIG. 2B. If the mass spectrometric analysis is performed for each of the 60 combinations of (CE value, m/z range) as mentioned earlier for one target compound, a total of 60 mass spectra in which different set of peaks are observed would be obtained (it should be noted that those mass spectra are not actually be created; they are mere examples of the spectrum waveforms that would be obtained if those mass spectra were created).

The spectrum data accumulator 81 accumulates the time-of-flight spectrum data which are sequentially fed for one target compound as described earlier. Consequently, time-of-flight spectrum data which cover a wide time-of-flight range corresponding to a wide mass-to-charge-ratio range of m/z 10-2000 are obtained. Those spectrum data contain information on the product ions generated by fragmentation under three different CE values of −10 V, −20 V and −30 V. After the time-of-flight spectrum data obtained through the N cycles of mass spectrometric analyses have been accumulated, the mass spectrum creator 82 creates a single mass spectrum based on the accumulated time-of-flight spectrum data (see FIG. 2C) and displays it, for example, on the screen of the display unit 92. In this mass spectrum, product ions can be observed over a wide mass-to-charge-ratio range of m/z 10-2000, and those product ions include various ions generated under the three different CE values.

This mass spectrum provides mass information of various fragments derived from one target compound. The mass information of those fragments can be used, for example, to identify partial structures and estimate the entire structure of the target compound. Obtaining an exhaustive set of information on the masses of various fragments facilitates the structural estimation as well as improves its accuracy.

In the MS/MS analysis mode in the previous embodiment, the MS/MS analysis is performed for all possible combinations of (CE value, m/z range) among the set CE values and m/z ranges. Such a method is advantageous in that product ions having a wide range of mass-to-charge ratios obtained under a plurality of levels of collision energy can be detected exhaustively, i.e. with no omission. However, if there is an m/z range within which no product ion is observed, the measurement performed for that range can be considered as a waste of time.

For example, if the fragmentation of at least some specific kind of compound more easily occurs under higher levels of collision energy and more easily generates product ions having lower mass-to-charge ratios, it is expected that combining a large CE value and a high m/z range will barely generate product ions. Accordingly, the MS/MS analysis for some combination of (CE value, m/z range) may be omitted if it is previously known or can be predicted that no significant product ion will be observed with that combination, rather than performing the MS/MS analysis for all combinations of (CE value, m/z range).

Figure 3A:
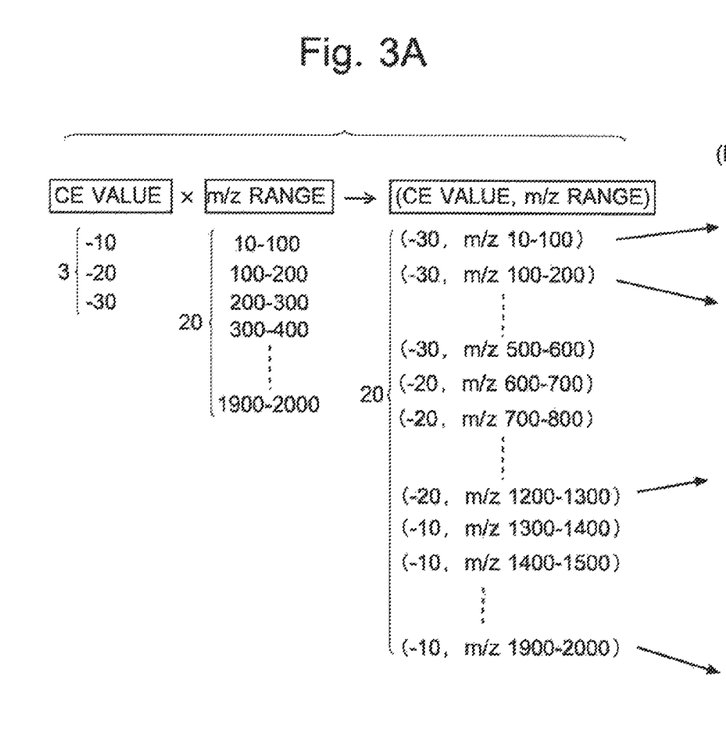
FIGS. 3A-3C are diagrams illustrating another example of the MS/MS analysis mode in the tandem mass spectrometer according to the present embodiment.
Figure 3B:
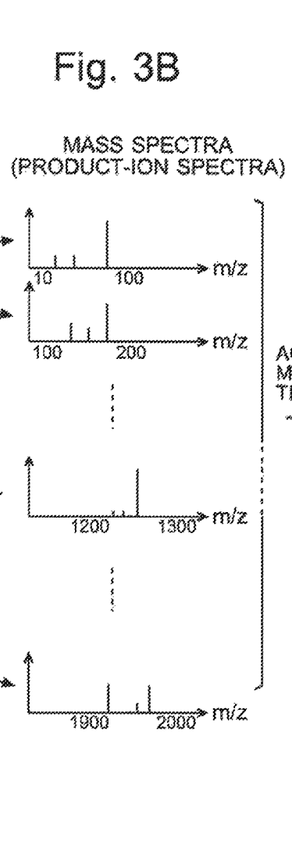
Figure 3C:
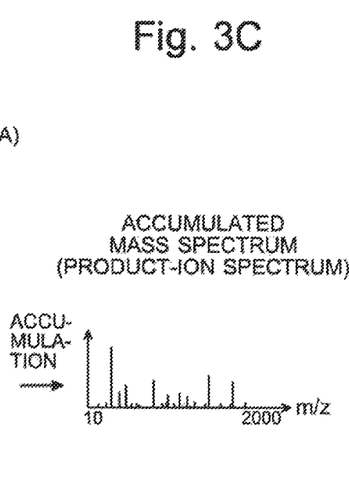

FIGS. 3A-3C are diagrams illustrating such an MS/MS analysis mode.

Although the CE values and m/z ranges are the same as those used in the example of the MS/MS mode analysis shown in FIGS. 2A-2C, the number of combinations of the CE value and m/z range is considerably reduced. This is achieved as follows: It can be assumed that at least some kind of compound will be more easily broken under larger CE values and easily generate product ions having smaller mass-to-charge ratios. Accordingly, the combinations of (CE value, m/z value) are determined in such a manner that the mass-to-charge-ratio range for the CE value of −30 V which gives the largest amount of collision energy be limited to m/z 10-600, the mass-to-charge-ratio range for the CE value of −20 V which gives the second largest amount of collision energy be limited to m/z 600-1300, and the mass-to-charge-ratio range for the CE value of −10 V which gives the smallest amount of collision energy be limited to m/z 1300-2000. The total number of combinations is thereby reduced to 20, which is one third of the total number of combinations in the MS/MS analysis mode shown in FIGS. 2A-2C. Accordingly, if the number N of cycles is the same as in the MS/MS analysis mode shown in FIGS. 2A-2C, the measurement time in the present case will be approximately reduced to one third. If the measurement time is the same, the number of cycles can approximately be tripled, which means a corresponding increase in the number of additions of the intensity of the same product ion and a consequent improvement of the sensitivity.

In the MS/MS analysis mode shown in FIGS. 3A-3C, each m/z range has only one level of collision energy combined. It is naturally possible to set two or more levels of collision energy for some of the m/z ranges. For example, the combinations of (CE value, m/z value) may be determined in such a manner that the mass-to-charge-ratio range for the CE value of −30 V which gives the largest amount of collision energy be limited to m/z 10-1000, the mass-to-charge-ratio range for the CE value of −20 V which gives the second largest amount of collision energy be limited to m/z 600-1500, and the mass-to-charge-ratio range for the CE value of −10 V which gives the smallest amount of collision energy be limited to m/z 1000-2000. In this case, the number of mass spectrometric analyses to be performed for one compound varies depending on the combination of (CE value, m/z range). This causes no problem in creating a mass spectrum for that compound.

In some cases, it may be previously known that an identification or structural analysis of a compound critically depends on whether or not a product ion having a specific mass-to-charge ratio is detected. One example is the case where a compound which may be one of the two different compounds "A" and "B" having approximately equal molecular weights can be identified as compound "A" if product ions "a" and "b" which respectively have specific mass-to-charge ratios are detected. In such a case, the number of mass spectrometric analyses to be performed under the combinations of (CE value, m/z range) corresponding to the m/z ranges which include those specific product ions may be given a greater value than the number of mass spectrometric analyses under the other combinations so that those product ions will be detected with a higher sensitivity.

For example, in the case where product ions having mass-to-charge ratios of 231 and 562 are essential for identifying a compound, the mass spectrometric analysis may be performed five times under each of the six (CE value, m/z range) combinations of (−10, m/z 200-300), (−20, m/z 200-300), (−30, m/z 200-300), (−10, m/z 500-600), (−20, m/z 500-600) and (−30, m/z 500-600), while the mass spectrometric analysis is performed two times under the other combinations of (CE value, m/z range). Such an adjustment of the number of executions of the mass spectrometric analysis to be reflected in one mass spectrum prevents the overlooking of the essential product ions while ensuring the acquisition of the mass information of the other product ions.

The tandem mass spectrometer in the previous embodiment has the configuration of a so-called Q-TOF mass spectrometer combined with a three-dimensional quadrupole ion trap. The present invention is also applicable in the configuration of a triple quadrupole mass spectrometer combined with an ion trap. Providing the ion trap for storing ions is not always necessary. For example, the ion guide 31 placed within the collision cell 3 may be provided with the ion storage function, or the orthogonal ion acceleration section in the time-of-flight mass analyzer 5 may also be provided with the ion storage function. The previously described characteristic analysis can similarly be performed using the ion storage function realized in this manner.

Any of the previously described embodiment and variations are a mere example of the present invention, and any change, addition or modification appropriately made within the spirit of the present invention in any aspect other than those already described will evidently fall within the scope of claims of the present application.

REFERENCE SIGNS LIST

1 . . . Ion Source
2 . . . Quadrupole Mass Filter
3 . . . Collision Cell
31 . . . Ion Guide
4 . . . Ion Trap
41 . . . Ring Electrode
42, 43 . . . Endcap Electrode
5 . . . Time-of-Flight Mass Analyzer
51 . . . Push-Out Electrode
52 . . . Grid Electrode
53 . . . Flight Space
54 . . . Reflector
55 . . . Ion Detector
61 . . . Q1 Driver
62 . . . CC Driver
63 . . . IT Driver
64 . . . TOF Driver
7 . . . Control Unit
71 . . . Analysis Condition Determiner
72 . . . Analysis Controller
8 . . . Data Processing Unit
81 . . . Spectrum Data Accumulator
82 . . . Mass Spectrum Creator
91 . . . Input Unit
92 . . . Display Unit

The invention claimed is:

1. A tandem mass spectrometer comprising:
an ion source configured to ionize a compound in a sample;
a first mass separation section configured to select, as a precursor ion, an ion having a specific mass-to-charge ratio from various kinds of ions generated by the ion source;

an ion fragmentation section configured to fragment the precursor ion by collision-induced dissociation; and a second mass separation section and a detector configured to perform a mass spectrometric analysis of various product ions generated by the fragmentation, wherein at least one from among the first mass separation section, the ion fragmentation section, and the second mass separation section is configured as an ion storage section that temporarily stores ions, or the tandem mass spectrometer further comprises a separate ion storage section that temporarily stores ions and that is placed between the first mass separation section and the ion fragmentation section or between the ion fragmentation section and the second mass separation section, the tandem mass spectrometer further comprising:

at least one processor, the at least one processor configured to:

a) change a collision energy imparted to the precursor ion in the collision induced dissociation in the ion fragmentation section to m levels, where m is an integer equal to or greater than two;

b) change a mass-to-charge-ratio range of the ions to be stored in the ion storage section or in the separate ion storage section to n ranges shifted along a mass-to-charge-ratio direction (where n is an integer equal to or greater than two);

c) set one of the m levels of collision energy, set one of the n mass-to-charge-ratio ranges, perform a mass spectrometric analysis of the product ions for a predetermined precursor ion under a condition including the combination of the set level of collision energy and the set mass-to-charge-ratio range, and perform the mass spectrometric analysis of the product ions at least one time for each of the m×n different combinations of the collision energy and the mass-to-charge-ratio range; and d) accumulate a spectrum data obtained by the mass spectrometric analysis of the product ions performed at least m×n times, and create one mass spectrum over a predetermined mass-to-charge-ratio range.

2. The tandem mass spectrometer according to claim 1, wherein:

the second mass separation section is a time-of-flight mass analyzer.

3. The tandem mass spectrometer according to claim 1, wherein:

the at least one from among the first mass separation section, the ion fragmentation section, and the second mass separation section is configured as the ion storage section that temporarily store ions.

4. A tandem mass spectrometer comprising:

an ion source configured to ionize a compound in a sample;

a first mass separation section configured to select, as a precursor ion, an ion having a specific mass-to-charge ratio from various kinds of ions generated by the ion source;

an ion fragmentation section configured to fragment the precursor ion by collision-induced dissociation; and a second mass separation section and a detector configured to perform a mass spectrometric analysis of various product ions generated by the fragmentation, wherein at least one from among the first mass separation section, the ion fragmentation section, and the second mass separation section is configured as an ion storage section that temporarily stores ions, or the tandem mass spectrometer further comprises a separate ion storage section that temporarily stores ions and that is placed between the first mass separation section and the ion fragmentation section or between the ion fragmentation section and the second mass separation section, the tandem mass spectrometer further comprising:

at least one processor, the at least one processor configured to:

a) change a collision energy imparted to the precursor ion in the collision induced dissociation in the ion fragmentation section to m levels, where m is an integer equal to or greater than two;

b) change a mass-to-charge-ratio range of the ions to be stored in the ion storage section or the separate ion storage section to n ranges shifted along a mass-to-charge-ratio direction (where n is an integer equal to or greater than two);

c) set one of the m levels of collision energy, set one of the n mass-to-charge-ratio ranges, perform a mass spectrometric analysis of the product ions for a predetermined precursor ion under a condition including the combination of the set level of collision energy and the set mass-to-charge-ratio range, combine each of the m levels of collision energy with an integer number of mass-to-charge-ratio ranges fewer than n among the n mass-to-charge-ratio ranges in such a manner that each of the n mass-to-charge-ratio ranges is selected at least one time, and perform the mass spectrometric analysis of the product ions at least one time for each of all combinations whose number is equal to or greater than m or n, whichever is greater; and d) accumulate spectrum data obtained by the mass spectrometric analysis of the product ions performed the number of times equal to or greater than m or n, whichever is greater, and create one mass spectrum over a predetermined mass-to-charge-ratio range.

5. The tandem mass spectrometer according to claim 4, wherein:

the second mass separation section is a time-of-flight mass analyzer.

6. The tandem mass spectrometer according to claim 4, wherein:

the at least one from among the first mass separation section, the ion fragmentation section, and the second mass separation section is configured as the ion storage section that temporarily store ions.

* * * * *